United States Patent [19]

Chene

[11] Patent Number: 4,874,846

[45] Date of Patent: Oct. 17, 1989

[54] PROCESS FOR THE PREPARATION OF ARYLOXYBENZOIC ACIDS CONTAINING A SULFONAMIDE GROUP

[75] Inventor: Alain Chene, Lyon, France

[73] Assignee: Rhone-Poulenc Agrochimie S.A., Lyon, France

[21] Appl. No.: 54,411

[22] Filed: May 26, 1987

Related U.S. Application Data

[63] Continuation of Ser. No. 563,033, Dec. 19, 1983, abandoned.

[30] Foreign Application Priority Data

Dec. 17, 1982 [FR] France .................................. 82 21509
Feb. 17, 1983 [FR] France .................................. 83 02807

[51] Int. Cl.$^4$ .............................................. C07B 45/04
[52] U.S. Cl. ..................................... 534/560; 534/558; 534/564; 534/751; 534/886; 546/24; 546/261; 546/284; 546/287; 546/288; 546/290; 546/291; 546/292; 549/6; 549/61; 549/63; 549/64; 549/65; 558/13; 558/192; 558/193; 558/190; 558/386; 558/392; 558/413; 560/12; 560/13; 560/138; 560/251; 560/252; 560/302; 562/430; 562/873; 562/15; 564/39; 564/49; 564/82; 564/83; 564/97; 564/91; 564/99; 552/8

[58] Field of Search .................... 564/91, 99, 39, 49, 564/82, 83, 97; 534/560, 558, 564, 751, 886; 546/24, 261, 284, 287, 288, 290, 291, 292; 549/6, 61, 63, 64, 65; 260/349, 545 R, 502.4 R; 558/13, 192, 193, 190, 386, 392, 413; 560/12, 13, 138, 257, 252, 302; 562/430

[56] References Cited

U.S. PATENT DOCUMENTS

| | | | |
|---|---|---|---|
| 3,471,559 | 10/1969 | Scherrer | 564/99 |
| 3,622,626 | 11/1971 | Moore | 71/103 X |
| 4,285,723 | 8/1981 | Cartwright et al. | 564/99 X |
| 4,447,634 | 5/1984 | Lee | 564/87 |
| 4,465,508 | 8/1984 | Barton et al. | 71/103 |
| 4,495,365 | 1/1985 | Dallos | 564/91 |

FOREIGN PATENT DOCUMENTS

| | | |
|---|---|---|
| 23100 | 1/1981 | European Pat. Off. . |
| 23392 | 2/1981 | European Pat. Off. . |
| 27837 | 5/1981 | European Pat. Off. . |
| 151943 | 11/1979 | Japan . |
| 106654 | 2/1982 | Japan . |

*Primary Examiner*—Charles F. Warren
*Assistant Examiner*—Carolyn S. Elmore
*Attorney, Agent, or Firm*—Morgan & Finnegan

[57] ABSTRACT

Process for the preparation of aryloxy-benzoic acids containing a sulphonamide group by the direct reaction of a phenoxy-benzoic acid with a sulphonamide, in the presence of a halogenating agent such as P(O)Cl$_3$.

26 Claims, No Drawings

PROCESS FOR THE PREPARATION OF ARYLOXYBENZOIC ACIDS CONTAINING A SULFONAMIDE GROUP

This application is a continuation of copending U.S. patent application Ser. No. 563,033 filed Dec. 19, 1983, now abandoned, which claims priority to French application 82/21509 filed Dec. 17, 1982 and French application 83/02807 filed Feb. 17, 1983, both of which are incorporated herein by reference.

This invention relates to an improved process for preparing certain aryloxybenzoic acid derivatives containing a sulfonamide group and having herbicidal properties.

More particularly, this invention relates to the preparation of a 3-(phenoxy)-N-sulfonylbenzamide comprising reacting the corresponding 3-phenoxybenzoic acid with a sulfonamide in the liquid phase in the presence of a halogenating agent. By "a 3-(phenoxy)-N-sulfonyl-benzamide" is meant a compound containing this moiety although there may be other substituents present on the phenoxy ring and or the benzamide ring. This invention further relates to the preparation of compounds of the formula:

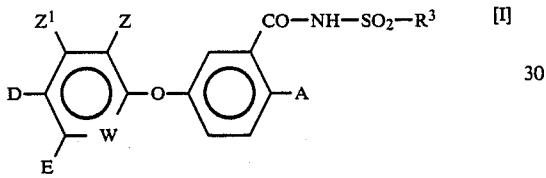

and their salts, in which formula:

A is selected from: hydrogen; fluorine; chlorine; bromine; iodine; nitro; —N=NCF$_3$; PO$_3$H$_2$ and its alkyl esters (said alkyl group having from 1 to 4 carbon atoms); NH$_2$; NHOH; N$_2$+; a carboxyl group or one of its functional derivatives (exemplified by, but not limited to alkyl esters, amides and salts); a monoalkylamino or dialkylamino group; NH—CC—R$^1$, wherein R$^1$ is selected from the group consisting of an alkyl radical, alkoxy radical, a monoalkylamino or a dialkylamino group; an alkyl group, a trialkylammonium group; NHSO$_2$R$^2$ wherein R$^2$ is selected from alkyl and phenyl; NHCONHSO$_2$R$^2$ in which R$^2$ has the meaning already indicated; an alkylthio group; an alkylsulphinyl group; an alkylsulphonyl group; a dialkylsulphonyl group; a cyanosulphonyl group; a hydroxyl group; an alkanoyloxy group; an alkoxy group; an alkoxy group substituted by alkoxycarbonyl; SH; a nitroso group; —SCN; an azide group; CF$_3$;

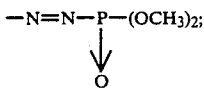

and an acyl group;

Z is selected from: hydrogen; fluorine; chlorine; bromine; iodine; an alkyl group; an alkoxy group; an alkylsulphinyl group; an alkylsulphonyl group; CF$_3$; NO$_2$; cyano; NH$_2$; NHCOR$^1$ group in which R$^1$ is defined as above; and CONH$_2$; wherein the alkyl moieties in groups defining Z preferably contain one to four carbon atoms;

Z$^1$ is selected from: hydrogen; halogen; an alkylamino group; and a dialkylamino group;

D is selected from: fluorine; chlorine; bromine; iodine; CF$_3$; an alkylthio group; an alkylsulphinyl group; an alkylsulphonyl group; a halogenoalkyl group; a sulphamoyl group; a formyl group; an alkylcarbonyl group; cyano; and a dimethylamino group;

E is selected from: hydrogen; a halogenoalkyl group; an alkoxy group; an alkylsulphinyl group; an alkylsulphonyl group; cyano; CF$_3$; NH$_2$; CONH$_2$; and NH—CO—R$^1$, R$^1$ having the meaning already indicated;

W is selected from: trivalent nitrogen, and —C(G)=;

G has one of the meanings given for Z; and

R$^3$ is selected from: a phenyl group, a pyridyl group, and a thienyl group, wherein said groups are optionally substituted by one or more halogen atoms, alkyl or nitro groups; an alkenyl or alkynyl radical having two to four carbon atoms; alkyl radical having one to four carbon atoms, said alkyl group being optionally substituted with one or more moieties selected from fluorine, chlorine, bromine, or iodine, and, preferably, trifluoromethyl or by one or more of the following substituents: carboxyl, alkoxycarbonyl (having two to five carbon atoms), alkylcarbonyl (having two to five carbon atoms), monoalkylcarbamoyl or dialkylcarbamoyl (said alkyl moieties having from one to four carbon atoms), alkylthio, alkylsulphinyl, alkylsulphonyl, each having from one to four carbon atoms, alkyl carbonyloxy (having two to five carbon atoms), alkylcarbonylamino (having two to five carbon atoms), or cyano; wherein, unless otherwise specified the alkyl or hydrocarbon moieties in the groups defining A, R$^1$, R$^2$, Z, Z$^1$, D, E, W, G, R$^3$, preferably contain one to four carbon atoms.

BACKGROUND OF THE INVENTION

Phenoxybenzoic acid derivatives containing a sulfonamide group are known to have herbicidal properties. Some of these derivatives are described in European Patent Application Nos. 3,416 and 23,392, Japanese Patent Application No. 82/106,654 and U.S. Pat. No. 4,285,723 These references describe methods of making certain compounds falling within formula (I) above, by reacting, at a temperature between 25° and 140° C., an intermediate acid halide of the formula:

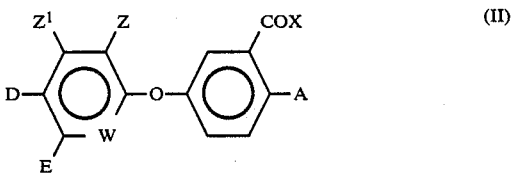

in which X is chlorine, bromine or iodine and A, Z, Z$^1$, D, E and W have the meanings already indicated, with a sulphonamide of the formula:

R$^3$SO$_2$NH$_2$ (III)

in which R$^3$ has the meaning already indicated, generally in the presence of an acid acceptor, in particular a tertiary amine such as N,N-dimethylaniline or pyridine, an alkali metal carbonate such as anhydrous potassium carbonate or an alkali metal fluoride such as caesium fluoride.

The compounds of the formula (I) can then be alkylated in any manner known to those of ordinary skill in the art. This may be accomplished by a reaction with a diazoalkane having one to four carbon atoms, so as to give the corresponding products substituted on the nitrogen atom of the sulphonamide group by an alkyl group having one to four carbon atoms; the hydrogen atom on this same nitrogen atom can also be replaced by alkali metal atoms for example, sodium, by reacting with basic alkali metal reagents.

It has been found that this known process for condensing the products of formulae (II) and (III) has various disadvantages, in particular, mediocre yields. It is considered that, in general, this is due to the presence of the acid acceptor, which lowers the yield by promoting a diacylation reaction. Furthermore, the use of an acid acceptor makes the isolation and purification of the final products more difficult and more expensive.

Another disadvantage of the known process is that it requires an additional reaction step to obtain the acid halide of the formula (II) from the corresponding acid of the formula.

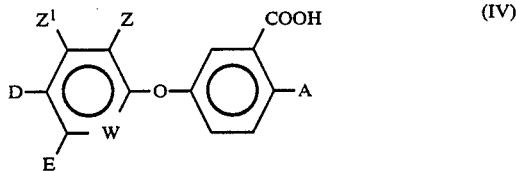

(IV)

One object of the invention is to overcome the disadvantages of the known processes.

Another object of the invention is to make it possible to prepare compounds of the formula (I) from technical-grade or industrial-grade reactants of the formula (IV).

In practice, the latter problem is all the more important because this type of acid is capable of containing a considerable number of impurities as a result of the number and nature of the reactions used to manufacture it. Thus, by way of non-limiting example, acifluorfen, having the formula:

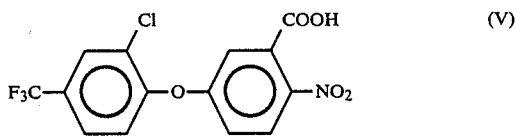

(V)

can be prepared by coupling an alkali metal meta-cresolate with a 3,4-dihalogenotrifluoromethylbenzene, followed by oxidation of the $CH_3$ group to a carboxylic acid group and then nitration. During a reaction sequence of this type, the number of isomers and other undesirable compounds progressively increases and, in acifluorfen of ordinary grade, it is common to detect a large number of acids, more particularly: 2-nitro-3-[2'-chloro-4'-(trifluoromethyl)-phenoxy]-benzoic acid in an amount which can easily reach 16% by weight, 2-nitro-5-[2'-chloro-5'-(trifluoromethyl)-phenoxy]-benzoic acid and 4-nitro-5-[2'-chloro-4'-(trifluoromethyl)-phenoxy]-benzoic acid, it easily being possible for these last two acids to be present in amounts ranging up to 3% by weight, together with a series of other acids in amounts which can also range up to 3%, this amount frequently being lower, however, e.g., less than 0.5%, such as e.g., 3-[2'-chloro-5'-(-trifluoromethyl)-phenoxy]-benzoic acid, 3-[2'-chloro-4'-(trifluoromethyl)-phenoxy]-benzoic acid and 2,4-dinitro-5-[2'-chloro-4'-(trifluoromethyl)-phenoxy]-benzoic acid, as well as 4-[2'-chloro-4'-(trifluoromethyl)-phenoxy]-nitrobenzene and 2-nitro-5-[2'-chloro-4'-(trifluoromethyl)-phenoxy]-toluene.

It is, therefore, an object of this invention to provide a process for making the desired end products with high purity and high yield from compounds of formula (IV) of low purity.

It is another object of this invention to provide a process for preparing the desired end product having high purity and high yield from technical grade or industrial grade starting reactant.

It is a further object of this invention to provide a process for preparing the desired end product without using an acid acceptor.

It is a still further object of this invention to provide a process for making the desired end products in as fews steps as possible.

Other advantages will become apparent in the course of the discussion which now follows.

BRIEF SUMMARY OF THE INVENTION

It has now been found that these objects can be wholly or partly achieved by virtue of the process of this invention, which comprises reacting an acid compound having formula (IV) with a sulphonamide of the formula (III). Whereby this process is carried out in the liquid phase, in the presence of a halogenating agent, preferably a chlorinating agent, and at a temperature such that the hydracid or hydrohalic acid which forms during the reaction is removed progressively, and in gaseous form, from the reaction medium.

The process of this invention is carried out in the absence of an acid acceptor. The presence of a solvent in addition to the reactants is optional.

DETAILED DESCRIPTION OF THE PREFERRED EMBODIMENTS

This process can be used to produce compounds of the formula:

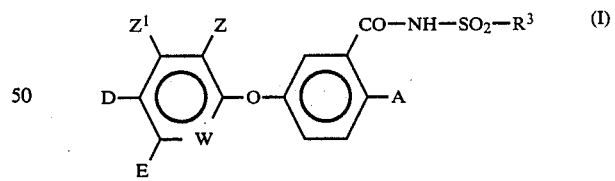

(I)

wherein A, R, $R^1$, $R^2$, $R^3$, Z, $Z^1$, W, D, E, F and G are as defined above.

A preferred embodiment of the present invention is utilizing the process of the present invention to produce sub-family compounds within Formula I wherein: A is selected from hydrogen, nitro, or chlorine; Z is halogen or more preferably chlorine; $Z^1$, E and G are hydrogen; D is trifluoromethyl; $R^3$ is alkyl most frequently having one to four carbon atoms, especially methyl; and W is —CH=.

According to a variant of the invention, the acid of the formula (IV) used in the process of this invention can contain up to 20% by weight and possibly up to 30% of impurities, mainly products having a similar formula to that of the principal reactant, but differing especially in the number and position of the substituents. These impurities are therefore essentially compounds containing the group

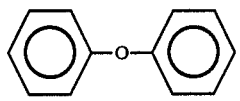

substituted in the various ways, or even the group

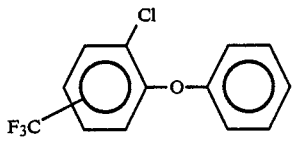

substituted in various ways.

The preferred reactants of the formulae (III) and (IV) are obviously chosen in such a way that the symbols present in their formulae have similar meanings to those which have just been given for the products of the formula (I).

Halogenating agents known to those skilled in the art may be used in this reaction, however it is preferable to use a chlorinating or brominating agent. Halogenating agents that contain a phosphorous or sulphoxide moiety are preferable. More preferably, the halogenating agent may be selected from: P(O)Cl$_3$, PCl$_3$, P(O)Br$_3$, PBR$_3$, SOCl$_2$, SO$_2$Cl$_2$. Most preferably, P(O)Cl$_3$ should be used.

The molar ratio of sulphonamide to acid compound is generally between 0.8 and 1.2. Preferably, said ratio should be between 0.9 and 1.1. Most frequently, these reactants are in stoichiometric proportions.

The molar ratio of the halogenating agent to acid generally varies between 0.1 and 5. It is preferably between 1 and 5. The halogenating agent can also serve as a solvent for the reaction. In this case, the molar ratio of halogenating agent to acid can exceed 5 and be as much as 20. The excess halogenating agent may be recovered from the reaction mixture by distillation after the reaction takes place for the purpose of subsequent recycling.

The reactants can also be dissolved in an inert solvent having a boiling point above the reaction temperature. Preferably, this solvent is a liquid aliphatic or aromatic hydrocarbon which may or may not be substituted by chlorine. Illustrative of such aromatic solvents are benzene, toluene, xylene, mixtures of xylenes and cumene which may or may not be substituted by chlorine. Further illustrative of solvents are chlorobenzene and 1,2-dichloroethane. It is also possible to use a mixture of several solvents. The use of an inert solvent has the practical advantage of permitting better heat transfer in an industrial-scale process. It also tends to avoid local overheating in the reaction medium. However, neither the solvent nor an excess of halogenating agent is necessary for the reaction to progress.

The temperature at which the process of this invention should be carried out is such that the acid halide or hydrohalic acid which is formed during the reaction is removed progressively from the reaction medium, in gaseous form, as it is generated. The reaction temperature is furthermore below the decomposition temperatures of the products of the formulae (III), (IV) and (I) involved in the process. When a solvent is used or if an excess of halogenating agent is used as the solvent, the temperature is advantageously less than or equal to the boiling point of the solvent or the halogenating agent. The reaction temperature should preferably be between 70° C. and 180° C. Where no solvent is used, the temperature is preferably between 80° C. and 120° C. In the presence of an inert solvent, especially in the case of cumene, which boils at 153° C., the temperature is advantageously maintained between 70° and 150° C.

At the end of the reaction, the compound of the formula (I) can be isolated by any method which is in itself known. The process according to this invention is distinguished by the simplicity of the method for recovery of the final product because this product is insoluble in the halogenating agent and this recovery therefore amounts essentially to filtration. Recovery also may be facilitated by adding a non-solvent, e.g. a liquid miscible with the reaction medium and in which the compound of Formula (I) is not soluble or has a low solubility.

The following examples illustrate the process of this invention are not intended to limit the scope of this invention.

EXAMPLE 1

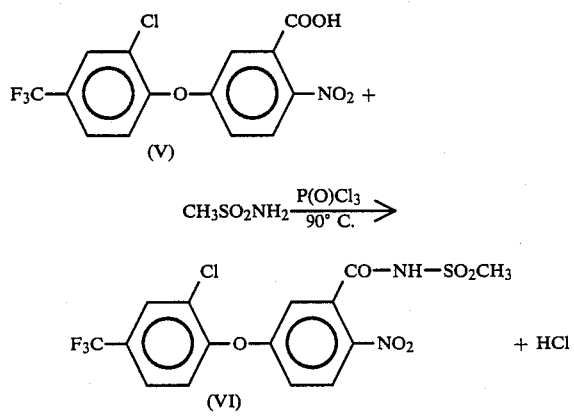

5-[2'-chloro-4'-(trifluoromethyl)-phenoxy]-2-nitrobenzoic acid (361.5 g; 1 mol) and methanesulphonamide (95 g; 1 mol) were suspended in P(O)Cl$_3$, i.e. phosphoryl chloride (300 cc; 3.22 mol). The reaction mixture was heated for 2 hours 15 minutes at 90 C., with stirring. Hydrogen chloride gas was evolved progressively from the reaction medium as it formed (in general, the heating can be stopped when the evolution of hydrogen chloride becomes uniform, the temperature then remaining at 90° C. by virtue of the reaction). After the addition of toluene (400 cc), the precipitate formed was filtered off and washed with toluene, then with methylene chloride and then with water.

This gave a white solid (393.2 g; 0.897 mol; yield: 90%) consisting of 5-[2'-chloro-4'-(trifluoromethyl)-phenoxy]-2-nitro-N-methanesulphonylbenzamide which melts at 221° C. The structure of this product was confirmed by infra-red and by nuclear magnetic resonance.

EXAMPLE 2

The same reaction was carried out as in Example 1.

The purity of the starting phenoxybenzoic acid was determined by high performance liquid chromatography (abbreviated to HPLC), a method of analysis known to those of ordinary skill in the art; the HPLC analysis was carried out under the following conditions:

the chromatography column was of length 20 cm and diameter 4 mm, packing of silica onto which was grafted a stationary phase containing an amine group (the chromatography is carried out by partition between the stationary phase and the eluent), the eluent consisted of a 42/40/18 mixture, in constant respective proportions by volume, of 2,2,4-trimethylpentane, propan-2-ol and acetic acid, the flow rate was 2 cc/minute.

The purity of the reaction product obtained by the method of this invention was also determined by HPLC under similar conditions, except that, in the eluent, the proportions of constituents in the eluent mixture were varied between the beginning and end of the chromatography from a ratio of 35/50/5 to 56/20/24 (elution gradient).

The accuracy of these chromatographic methods was checked by using standards corresponding to samples of each of the impurities mentioned, taken in isolation.

The percentages indicated below are percentages by weight. The "technical-grade" acid used contains:
80.9% of 5-[2′-chloro-4′-(trifluoromethyl)-phenoxy]-2-nitrobenzoic acid,
8.2% of 3-[2′-chloro-4′-(trifluoromethyl)-phenoxy]-2-nitro benzoic acid,
3.3% of 5-[2′-chloro-4′-(trifluoromethyl)-phenoxy]-4-nitro benzoic acid,
less than 1% of 5-[2′-chloro-5′-(trifluoromethyl)-phenoxy]-2-nitrobenzoic acid and
less than 1% of 3-[2′-chloro-4′-(trifluoro methyl)-phenoxy]-benzoic acid.

The technical-grade acid having the composition defined above (361.5 g) and methane sulphonamide (95 g; 1 mol) were suspended in P(O)Cl₃, i.e. phosphoryl chloride (300 cc or 3.22 mol). The reaction mixture was heated for 2 hours at 90° C., with stirring. Hydrogen chloride gas was evolved progressively from the reaction medium as it formed. Xylene (500 cc) was added before the mixture was cooled to 10°. The precipitate was filtered off, washed with xylene (200 cc), then with methylene chloride (800 cc) and finally with water (1,500 cc), and then dried in an oven.

This gave a white solid (277.4 g) consisting of 5-[2′-chloro-4′-(trifluoromethyl)-phenoxy]-2-nitro-N-methanesulphonylbenzamide, which melts at 221° C. The purity of this product, determined by HPLC, is 98%. The structure of this product was confirmed by infra-red and by nuclear magnetic resonance.

Taking into account the purity of the reactants and reaction product, the real yield of the operation is 77% of 5-[2′-chloro-4′-(trifluoromethyl)-phenoxy[-2-nitro-N-methanesulphonyl]benzamide, relative to the 5-[2′-chloro-4′-(trifluoromethyl)-phenoxy]-benzoic acid, of the formula (V), initially present.

EXAMPLE 3

The same reaction in Example 1, was carried out in toluene (750 cc) as the solvent, making it possible to obtain 5-[2′-chloro-4i-(trifluoromethyl)-phenoxy]-2-nitro-N-methanesulphonylbenzamide (324.5 g; 0.740 mol). The yield was 74%, of the formula (VI).

EXAMPLE 4

The same reaction as in Example 2 was carried out in 1,2-dichloroethane (1,500 cc) as the solvent, making it possible to obtain 5-[2′-chloro-4′-(trifluoromethyl)-phenoxy]-2-nitro N-methanesulphonylbenzamide (329 g). Its purity, determined by HPLC, is 95%.

Taking into account the purity of the reactants and reaction product, the real yield of the operation is 88% of 5-[2′-chloro-4′-(trifluoromethyl)-phenoxy]-2-nitro-N-methanesulphonylbenzamide, relative to the 5-[2′-chloro-4′-(trifluoromethyl)-phenoxy]-2-nitrobenzoic acid, initially present.

What is claimed is:

1. A process for preparing a 3-(phenoxy)-N-sulphonylbenzamide comprising reacting (i) the corresponding 3-phenoxybenzoic acid with (ii) a sulphonamide in liquid phase in the presence of a halogenating agent POCl₃, and in the absence of an acid acceptor, said reaction forming a hydrochloric acid and a 3-(phenoxy)-N-sulphonylbenzamide, said reaction taking place at a temperature such that the hydrochloric acid is removed progressively in gaseous form from the reaction medium as it is formed.

2. The process of claim 1 wherein said reactant (i) is a 2-nitro-5-(phenoxy) benzoic acid.

3. The process of claim 1 wherein said reactant (i) is 2-nitro-5-(2′-chloro-4′-trifluoromethylphenoxy)-benzoic acid.

4. A process for preparing an end product compound having the formula:

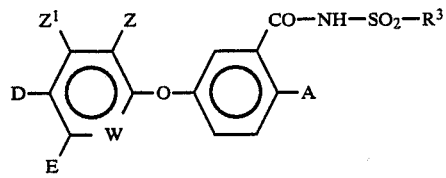

wherein:

A is selected from: hydrogen; fluorine; chlorine; bromine; iodine; nitro; —N=NCF₃; PO₃H₂; PO₃-alkyl, the alkyl group having from 1 to 4 carbon atoms; NH₂; NHOH; N⁺₂; a carboxyl group; a carboxylic alkyl ester; a carboxylic amide; a carboxylic salt; a monoalkylamino group; a dialkylamino group; NH—CO—R₁, wherein R¹ is selected from the group consisting of an alkyl radical, an alkoxy radical, a monoalkylamino group and a dialkylamino group; an alkyl group; a trialkylammonium group; NHSO₂R² where R² is selected from the group consisting of alkyl and phenyl; NHCONHSO₂R²; an alkylthio group; an alkylsulphinyl group; an alkylsulphonyl group; a cyanosulphonyl group; a hydroxyl group; an alkanoyloxy group; an alkoxy group; an alkoxy substituted by alkoxycarbonyl; SH; a nitroso group; —SCN; an azide group; CF₃;

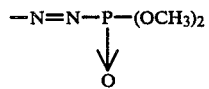

and an acyl group;

Z is selected from: hydrogen; fluorine; chlorine; bromine; iodine; an alkyl group; an alkoxy group; an alkylsulphinyl group; an alkylsulphonyl group; CF₃; NO₂; cyano; NH₂; NHCOR¹; and CONH₂;

Z¹ is selected from: hydrogen; halogen; an alkylamino group and a dialkylamino group;

D is selected from: fluorine; chlorine; bromine; iodine; an alkylthio group; an alkylsulphinyl group; an alkylsulphonyl group; a halogenoalkyl group; a sulphamoyl group; a formyl group; an alkylcarbonyl group; cyano; and a dimethylamino group;

E is selected from: hydrogen; a halogenoalkyl group; an alkoxy group; an alkylsulphinyl group; an alkylsulphonyl group; cyano; $NH_2$; $CONH_2$; and $NH-CO-R^1$;

W is selected from the group consisting of trivalent nitrogen, and $-C(G)=$;

G is selected from the group consisting of hydrogen; fluorine; chlorine; bromine; iodine; an alkyl group; an alkoxy group; an alkylsulphinyl group; an alkylsulphonyl group; trifluoromethyl; nitro; cyano; $NH_2$; $HNCOR^1$; and $CONH_2$;

$R_3$ is selected from the group consisting of substituted or unsubstituted phenyl, said substituents selected from the group consisting of one or more halogens, alkyl and nitro; unsubstituted or substituted pyridyl, said substituents selected from the group consisting of one or more halogens, alkyl and nitro; unsubstituted or substituted thienyl, said substituents selected from the group consisting of one or more halogens, alkyl and nitro; an alkenyl or alkynyl radical having two to four carbon atoms; an alkyl radical having one to four carbon atoms, said alkyl group being optionally substituted with one or more moieties selected from fluorine, chlorine, bromine, iodine, carboxyl, alkoxycarbonyl having two to five carbon atoms, alkylcarbonyl, having two to five carbon atoms, monoalkylcarbamoyl wherein said alkyl moeity has from one to four carbon atoms, dialkylcarbamoyl, wherein said alkyl moiety has from one to four carbon atoms, alkylthio having from one to four carbon atoms, alkylsulphinyl having from one to four carbon atoms, alkylsulphonyl, having from one to four carbon atoms, alkylcarboxyloxy having two to five carbon atoms, alkylcarbonylamino, having two to five carbon atoms, and cyano;

said process comprising reacting an acid compound having the formula:

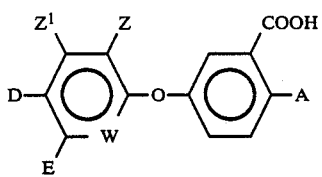

with a compound having the formula $R^3-SO_2-NH_2$ in the presence of a halogenating agent, $POCl_3$, and in the absence of an acid acceptor, wherein said reactants comprise a reaction medium having a liquid phase, said reaction forming the desired end product compound and hydrochloric acid in gaseous form, said reaction taking place at a temperature sufficient to cause the gaseous hydrochloric acid to leave progressively from the reaction medium as it is formed without causing the decomposition of the reactants.

5. The process according to claim 4 wherein A is selected from hydrogen, nitro and fluorine; Z is halogen, $Z^1$ and E are hydrogen, D is trifluoromethyl, and W is $-C=$.

6. The process of claim 4 wherein A is nitro.

7. The process of claim 4 wherein Z is chlorine and $R^3$ is alkyl.

8. The process of claim 4 wherein $R^3$ is methyl.

9. A process according to claim 1 wherein the source of the acid compound contains impurities.

10. A process according to claim 9 wherein the proportion of impurities in the acid compound is less than 30% by weight.

11. A process according to claim 9 wherein the impurities substantially comprise diphenyl ether compounds.

12. A process according to claim 9 wherein the impurities substantially comprise diphenyl ether compounds substituted on one phenyl ring by chloro in the 2-position and a trifluoromethyl group.

13. A process according to claim 1 wherein the molar ratio of the sulphonamide to the 3-phenoxybenzoic acid is between 0.8 and 1.2.

14. A process according to claim 1 wherein the molar ratio of the sulphonamide to the 3-phenoxybenzoic acid is between 0.9 and 1.1.

15. A process according to claim 1 wherein the molar ratio of the sulphonamide to the 3-phenoxybenzoic acid is stoichiometric.

16. A process according to claim 1 wherein the molar ratio of halogenating agent to the acid is between 1 and 5.

17. A process according to claim 1 wherein the reaction is carried out in the presence of an inert solvent.

18. A process according to claim 17, wherein the solvent is selected from the group consisting of a liquid aliphatic hydrocarbon and a liquid aromatic hydrocarbon.

19. A process according to claim 17 wherein the solvent is substituted by chlorine.

20. A process according to claim 1 wherein the reaction temperature is below the decomposition temperature of the reactants.

21. A process according to claim 17 wherein the reaction temperature is less than the boiling point of the solvent used.

22. A process according to claim 17 wherein the reaction temperature is equal to the boiling point of the solvent used.

23. A process according to claim 1, wherein the reaction temperature is between 70° C. and 180° C.

24. A process according to claim 1 wherein the reaction temperature is between 70° C. and 150° C.

25. A process according to claim 4 wherein D is $CF_3$.

26. A process according to claim 4 wherein E is $CF_3$.

* * * * *